United States Patent [19]

McManus et al.

[11] Patent Number: 4,956,490

[45] Date of Patent: Sep. 11, 1990

[54] PROCESS FOR PREPARING BENZYLPYRUVIC ACIDS AND ESTERS

[75] Inventors: James W. McManus, Leesburg; John F. Genus, Albany, both of Ga.

[73] Assignee: Merck & Co., Inc., Rahway, N.J.

[21] Appl. No.: 321,040

[22] Filed: Mar. 9, 1989

[51] Int. Cl.$^5$ ............................................. C07C 69/76
[52] U.S. Cl. .................................. 560/051; 560/023; 560/053; 562/434; 562/459; 562/463; 558/414
[58] Field of Search ................ 560/051, 023, 053; 562/434, 459, 463; 558/414

[56] References Cited

U.S. PATENT DOCUMENTS

| | | | |
|---|---|---|---|
| 3,520,934 | 0/1970 | Dunkel et al. | 260/599 |
| 4,474,692 | 10/1984 | Nishikawa et al. | 260/112.5 |
| 4,617,291 | 10/1986 | Martin et al. | 514/19 |

FOREIGN PATENT DOCUMENTS 0051391 12/1982 European Pat. Off.
3317290 11/1983 Fed. Rep. of Germany.

OTHER PUBLICATIONS

L. Weinstock, et al., Synth. Comm., (1(12), 943–946 (ENG) (1981).
E. D. Thorsett, Tetrahedron Letters, 23(18), 1987–1996 (Eng) (1982).
J. M. Domagala, Tetrahedron Letters, 21(52), 4997–5000 (1980).
Rylandert and Himelstein, Engelhard Ind. Tech. Bull., 4, 131 (1964).
T. W. Russel, et al., J. Org. Chem., 42, No. 3 (1977).
S. Kim, et al., J. Org. Chem., 50, No. 5, 560–565 (1985).

*Primary Examiner*—Paul J. Killos
*Attorney, Agent, or Firm*—Salvatore C. Mitri; Joseph F. DiPrima

[57] ABSTRACT

There is disclosed a continuous, non-isolation process for preparing benzylpyruvic acids and benzylpyruvic esters. The benzylpyruvic acids and esters obtained are useful as intermediates to prepare carboxyalkyl dipeptide compounds which are used as angiotension converting enzyme (ACE) inhibitors to treat hypertension.

29 Claims, No Drawings

PROCESS FOR PREPARING BENZYLPYRUVIC ACIDS AND ESTERS

SUMMARY OF THE INVENTION

A continuous, non-isolation process is provided for preparing benzylpyruvic acids and benzylpyruvic esters which are useful as intermediates in the preparation of carboxyalkyl dipeptides which are used as angiotension converting enzyme (ACE) inhibitors in the treatment of hypertension. (See, for example, U.S. Pat. Nos. 4,374,829 and 4,472,380). Since the process, if the invention is continuous and does not require the isolation of intermediate reaction products, it is more economical and results in obtaining the invention compounds in greater yield and at higher purity than has been possible with prior art processes.

In general, the continuous process of the invention comprises sequentially condensing an aryl aldehyde with a pyruvate; esterifying the $\beta,\gamma$-unsaturated $\alpha$-keto acid condensation product with an esterifying agent; and, selectively reducing only the olefinic portion of the unsaturated ester with hydrogen in the presence of a heterogeneous catalyst.

Use of the heterogeneous catalyst in the invention process results in total selectivity in reducing only the olefinic bond of the $\beta,\gamma$-unsaturated-$\alpha$-keto acids and esters. Prior art processes result in about a 25–35% reduction of the keto group to an alcohol which not only means a comparable yield reduction of 25–30%, but also requires more difficult and protracted purification methods. Thus, the invention process results in increased yields and avoids unwanted side reactions by reducing only the olefinic portions.

BACKGROUND OF THE INVENTION

Several prior art processes are known for preparing benzylpyruvates and derivatives thereof, but these processes either result in low product yields, require the use of uneconomical reagents, involve extensive processing steps, or present environmental and safety concerns.

For example, M. Kie, et. al., [Yiyao Gongye, 17(3), 99–101 (1988)] disclose a process where the benzylpyruvic condensation product is subjected to hydride reduction which results in reducing both the olefinic bond and the ketone function. This requires that the $\alpha$-hydroxy group be oxidized in order to regenerate the ketone. In this process, it is the saturated $\alpha$-keto acids that are subjected to esterification.

R. Barner, et. al., [U.S. Pat. No. 4,675,421 (1988)] disclose the preparation of hydroquinone derivatives used to produce d-$\alpha$-tocophenol and the preparation of various hydroquinone starting materials. Several examples disclose processes for preparing 4-aryl-2-ketobutanoic acids and esters by sequentially condensing substituted aryl aldehydes with pyruvic acid, catalytically reducing the $\beta,\gamma$-unsaturated-$\alpha$-keto acid salts with a Pd/C catalyst in an aqueous base and esterifying the reduction product with N,N'-carbonyldiimidazole (CDI) and a complex alcohol.

In the processes disclosed by R. Barner, et. al., for preparing the ketobutanoic acids and esters, the condensation reaction is run in alcoholic KOH at reflux temperatures thereby limiting the processes to aryl aldehydes which are deactivated by substitution with alkoxy and alkyl groups. In addition, the esterification steps utilize only saturated $\alpha$-keto acids which require the use of relatively costly coupling agents (e.g., CDI) to achieve good yields. The use of costly coupling agents may be justified when coupling equally costly alcohols and acids, but they become uneconomical when lower alkyl compounds are prepared such as those of the present invention.

M. Reimer [J. Am. Chem. Soc. 46 (1924)] discloses a process for synthesizing methyl and ethyl benzalpyruvate by condensing pyruvic acid and benzalaldehyde in water in the presence of sodium hydroxide; isolating and drying the sodium salt of benzalpyruvic acid; redissolving and reprecipitating the salt as the free acid; and, esterifying the thusly isolated acid by conventional Fisher esterification. The $\beta,\gamma$-unsaturated-$\alpha$-keto ester product was obtained in low yields and low purity.

DETAILED DESCRIPTION OF THE INVENTION

The continuous, non-isolation process of the invention can be used to prepare benzylpyruvic acids and esters having the formula:

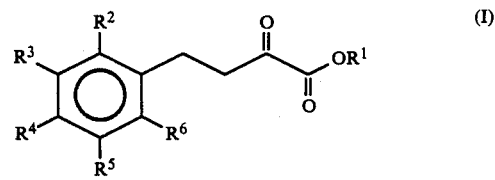

wherein:
$R^1$ is H or straight chain or branched $C_1$–$C_4$ alkyl; and,
$R^2$–$R^6$ can be the same or different and are H, $C^1$–$C^6$ alkyl, aryl, halo, nitro, hydroxy, alkoxy, phenoxy or nitrile.

In general, the continuous, non-isolation process of the invention comprises sequentially condensing an aryl aldehyde with a pyruvate to obtain an unsaturated $\alpha$-keto acid; esterifying said unsaturated $\alpha$-keto acid with a $C_1$–$C_4$ alkyl chloroformate to obtain an unsaturated $\alpha$-keto ester; and, reducing said unsaturated $\alpha$-keto acid or said unsaturated $\alpha$-keto ester with hydrogen in the presence of a heterogeneous catalyst to obtain compounds of formula I.

Illustrative of the $R^2$–$R^6$ aryl substituents that can be used in the present invention are phenoxy, substituted phenyl, phenyl-NHCO-alkyl and phenyl-NHCO-phenyl.

Typical condensing agents that can be used in the process of the invention are potassium hydroxide, sodium hydroxide and calcium hydroxide.

The pyruvates that can be used are the pyruvates of potassium, sodium or calcium, preferably sodium pyruvate.

Of the $C_1$–$C_4$ alkyl chloroformates that can be used, ethyl chloroformate is preferred.

Each of the condensation, esterification and reduction portions of the process are carried out in a suitable solvent such as water, chloroform, ethanol, ethyl acetate, methylene chloride, and the like. Except for the esterification step where protic solvents can not be used, the solvent selected is not critical.

For greater efficiency, higher yield and better purity, the esterification portion of the process can be carried out under an inert atmosphere such as, for example, argon or nitrogen and the reduction portion can be carried out under a pressure of from about 5–30 p.s.i., preferably 10–15 p.s.i.

Generally, the process of the invention can be completed in about 15–20 hours depending upon the temperature at which the process is carried out. The process temperature employed is, in turn, somewhat dependent upon whether the $R^2$–$R^6$ substituents are electron donating groups (such as hydroxy, alkyl, alkoxy, phenoxy and aryl) or whether these substituents are hydrogen or electron withdrawing groups (such as halo (I, Cl, Br) nitro and nitrile. When the $R^2$–$R^6$ substituents are electron donating groups, temperatures of about 10°–25° C. can be used because the aldehyde is less reactive. When the $R^2$–$R^6$ substituents are hydrogen or electron withdrawing groups, lower temperatures of about 0°–5° C. are used to accommodate the more reactive aldehyde.

While it may be possible to use homogeneous catalysts in the process of the invention, heterogeneous catalysts are preferred. In addition to being costly, homogeneous catalysts dissolve in the reaction mixture and are generally difficult to separate from the desired product. Heterogeneous catalysts, on the other hand, do not dissolve in the reaction mixture so that the desired product is quickly and easily obtained. Although many other heterogeneous catalysts can be used in the invention process, palladium hydride is preferred as it is relatively easy and inexpensive to produce and permits the selective reduction of only the olefinic portion of the β,γ-unsaturated-α-keto esters and acids. Other heterogeneous catalysts such as Pd/C do not exhibit this selectivity typically resulting in significant reduction of the ketone group as well as the olefin.

For some commercial applications, it may be desirable to stop the process after esterification and recover the unsaturated α-keto ester. This can be readily accomplished by recovering the unsaturated α-keto ester by evaporating the solvent (70–100 mm $H_2$ and 25°–75° C.) and then purifying the ester, if desired, by vacuum distillation using a short-path wiped film evaporator (WFE) apparatus.

The process of the invention is further illustrated in the following reaction scheme.

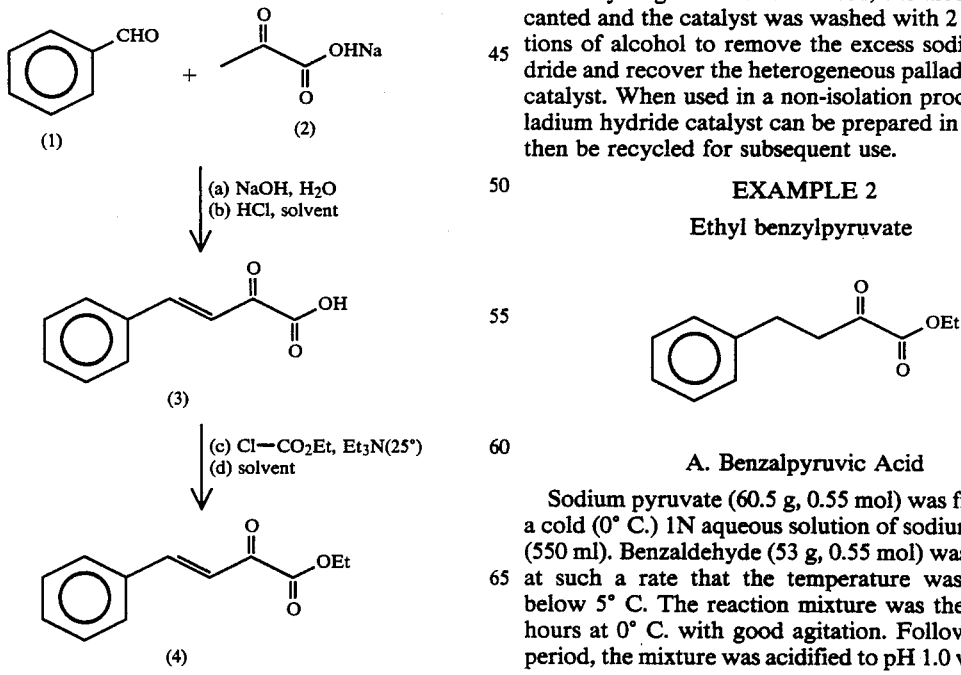

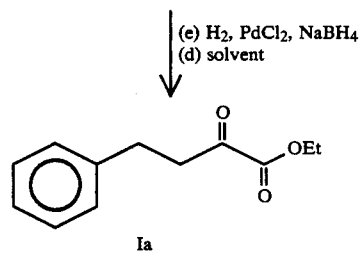

As shown in the reaction scheme, benzaldehyde (1) is reacted with sodium pyruvate (2) in the presence of aqueous sodium hydroxide. After aging, the pH of the reaction mixture is adjusted with HCl and solvent (ethyl acetate) is added. Water is then azeotropically removed from the reaction mixture to obtain benzalpyruvic acid (3) in solution. Benzalpyruvic acid (3) is treated with triethylamine ($Et_3N$) and ethyl chloroformate (Cl—$CO_2Et$) at 25° C. After removal of triethylamine hydrochloride and separation of aqueous layers, unsaturated benzalpyruvic ester (4) is obtained. Treatment of the unsaturated benzalpyruvic ester (4) with heterogeneous catalyst ($PdCl_2$, $NaBH_4$) in the presence of hydrogen affords ethyl benzylpyruvate (Ia).

Details of the process of the invention and the manner in which it can be practiced are provided in the following examples. It should be noted that while Examples 2–4 below are presented as step-wise processes, they were actually carried out continously without isolating intermediates. Samples of the intermediates shown in these examples were removed during processing to identify them and to monitor the progress of the reactions.

EXAMPLE 1

Preparation of Heterogeneous Palladium Hydride Catalyst

Palladium chloride (0.13 g) was reacted in 10 ml alcohol with sodium borohydride (0.05 g, 1.3 mmol). When hydrogen evolution ceased, the alcohol was decanted and the catalyst was washed with 2×10 ml portions of alcohol to remove the excess sodium borohydride and recover the heterogeneous palladium hydride catalyst. When used in a non-isolation process, the palladium hydride catalyst can be prepared in situ and can then be recycled for subsequent use.

EXAMPLE 2

Ethyl benzylpyruvate

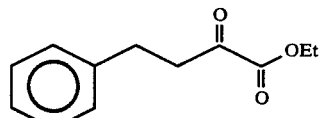

A. Benzalpyruvic Acid

Sodium pyruvate (60.5 g, 0.55 mol) was first added to a cold (0° C.) 1N aqueous solution of sodium hydroxide (550 ml). Benzaldehyde (53 g, 0.55 mol) was then added at such a rate that the temperature was maintained below 5° C. The reaction mixture was then aged four hours at 0° C. with good agitation. Following the age period, the mixture was acidified to pH 1.0 with 6N HCl maintaining a temperature of 0°–5° C. After acidification, the benzalpyruvic acid product was extracted with 500 ml ethyl acetate. Yield: 75–77% by HPLC analysis. Anal. Calcd. for $C_{10}H_7O_3K$: C, 56.08; H, 3.30; K, 18.21. Found: C, 56.11; H, 3.31; K, 18.20. $^1H$ NMR (acetone-$d_6$) δ: 7.2 (d, 1H), 7.8 (d, 1H), 7.5 (s, 5H). IR (KBr) cm$^{-1}$: 3500sb, 3050–2900s, 1740s, 1695s, 1230s, 1020s.

B. Ethyl Benzalpyruvate

To the benzalpyruvic acid of step A in water-saturated ethyl acetate there was added triethylamine (56.2 g, 0.55 mol) at a rate less than 0.5 ml/min with good agitation. Water was then azeotropically removed by vacuum distillation and the benzalpyruvic acid concentration readjusted to 120 g/l with dry ethyl acetate. Ethyl chloroformate (59.7 g, 0.55 mol) was then added over a one hour period at 20°–25° C. followed by a one hour age. The mixture was cooled to 0°–5° C. and quenched with 350 ml of cold water. The aqueous layer was discarded and the organic layer was washed with cold (0°–5° C.) 5% sodium bicarbonate solution (350 ml) followed by cold (0°–5° C.) 5% sodium chloride (350 ml). The ethyl acetate was removed by vacuum concentration affording crude ethyl benzalpyruvate in a yield of 95–97%. The ester was subsequently purified by distillation using a short-path wiped film evaporator (WFE) apparatus (150° C., 0.1 mm Hg).

Distillation yield: 94%. Anal. Calcd. for $C_{12}H_{12}O_3$: C, 70.57; H, 5.92. Found: C, 70.60; H, 5.97. $^1H$ NMR (CDCl$_3$) δ: 1.3 (t, 3H), 4.2 (q, 2H), 6.9 (d, 1H), 7.4 (d, 1H), 7.2 (s, 5H). IR (film) cm$^{-1}$: 3100m, 1740s, 1600s, 1070s.

C. Ethyl Benzylpyruvate

The ethyl benzalpyruvate of step B (70 g, 0.35 mol) was added to 450 ml of a suitable solvent (ethyl acetate) followed by addition of the heterogeneous palladium hydride catalyst (Example 1) at a 1:500 ratio.

The reactor was pressurized with H to 10 psi for a two hour period or until hydrogen uptake ceased. The catalyst was then removed by filtration and the ethyl benzylpyruvate product isolated in 98% yield and comparable purity by evaporation of the solvent under vacuum. Anal. Calcd. for $C_{12}H_{14}O_3$: C, 69.91; H, 6.85. Found: C, 69.95; H, 6.85. $^1H$ NMR (CDCl$_3$) δ: 1.3 (t, 3H), 3.0 (m, 4H), 4.2 (q, 2H), 7.2 (s, 5H). IR (film) cm$^{-1}$: 3450w, 3100s, 1750s, 1725s, 1600m, 1300–1150s, 1075s.

EXAMPLE 3

Ethyl 4-(p-Chlorophenyl)-2-Ketobutanoate

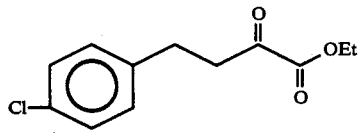

A. p-Chlorobenzalpyruvic Acid

Sodium pyruvate (24.2 g, 0.22 moL) was added to a cold (0° C.) solution of 1N sodium hydroxide (200 mL) and ethanol (10 mL). p-Chlorobenzaldehyde (28.11 g, 0.20 moL) was then added, maintaining the temperature below 5° C. The reaction mixture was aged six hours at 0°–5° C. and then allowed to warm to 20° C. where it was aged an additional six hours to effect complete reaction. The mixture was cooled to −10° C. and the pH adjusted to 1.0 with cold 6N HCl. The p-chlorobenzalpyruvic acid product was then extracted with 800 mL ethyl acetate in 94% yield.

B. Ethyl p-Chlorobenzalpyruvate

To the p-chlorobenzalpyruvic acid from step A in wet ethyl acetate was added triethylamine (11.1 g, 0.11 moL) at a rate less than 0.5 mL/min followed by azeotropic removal of water. Ethyl chloroformate (11.9 g, 0.11 moL) was then added at room temperature over a one hour period and the batch aged one hour to effect complete reaction. Workup followed, as in Example 1, to afford ethyl p-chlorobenzalpyruvate in 99% yield.

C. Ethyl p-Chlorobenzylpyruvate

To the ethyl p-chlorobenzalpyruvate from step B (23.6 g, 0.1 moL) was added 0.1 g of the palladium catalyst from Example 1. The reactor was pressurized to 10 psi with H$_2$ for two hours after which time the catalyst was removed by filtration and the ethyl 4-(p-chlorophenyl)-2-ketobutanoate isolated by vacuum concentration in quantitative yield. $^3H$ NMR (CDCl$_3$) δ: 1.1 (t, 3H), 3.8 (m, 4H), 4.0 (q, 2H), 7.1 (s, 4H), IR (film) cm$^{-1}$: 3450w, 3075–2875s, 1750s, 1710s, 1600m, 675s.

EXAMPLE 4

Ethyl 4-(p-Methoxyphenyl)-2-Ketobutanoate

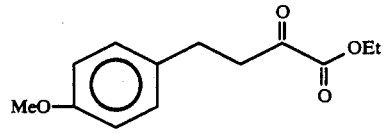

A. 4-(p-Methoxyphenyl)-2-Oxo-3-Butenoic Acid

Sodium pyruvate (24.2 g, 0.22 mol) was dissolved in 200 ml 1N aqueous sodium hydroxide at 20° C. To this solution there was added anisaldehyde (27.4 g, 0.20 mol) at 0.2 ml/min. The solution was aged twenty-four hours at 20° C., cooled at 0° C. and acidified with 6N NCl to pH 1.0 while maintaining a temperature of 0° C. The 4-(p-methoxyphenyl)-2-oxo-3-butenoic acid product was then extracted with 500 ml ethyl acetate and isolated as a yellow solid by concentration under vacuum. The yield by HPLC analysis was 88%.

B. Ethyl-4-(p-Methoxyphenyl)-2-Ketobutanoate

The unsaturated keto acid from step A was then esterified and reduced as in Examples 2 and 3 to afford ethyl 4-(p-methoxyphenyl)-2-ketobutanoate in essentially quantitative yield. $^1H$ NMR (CDCl$_3$) δ: 1.3 (t, 3H), 3.0 (m, 4H), 3.7 (q, 2H), 7.2 (dd, 4H). IR (film) cm$^{-1''}$ 3475. 3100–2050. 1695. 1750. 1600. 1300, 1150, 750.

EXAMPLE 5

4-Phenyl-2-Ketobutanoic Acid

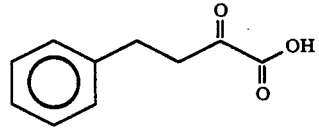

Benzalpyruvic acid (2-oxo-4-phenyl-3-butenoic acid) prepared as in step B of Example 2 (26.4 g, 0.15 mol) was dissolved in 150 ml ethanol. The catalyst from Example 1 was then added to the unsaturated acid. The reactor was pressurized to 10 psi with hydrogen and aged with good agitation for two hours. The catalyst was then removed by filtration and the titled product isolated in quantitative yield following vacuum concentration. $^1$H NMR (CDCl$_3$, DMSO-d$_6$) δ: 3.9 (m, 4H), 7.3 (s, 5H), 10.9 (s, 1H). IR (KBr) cm$^{-1}$: 3500m, 3000m, 1725s, 1700s, 1600m, 1200s, 970m.

What is claimed is:

1. A continuous, non-isolation process for preparing benzylpyruvic acids and esters having the formula:

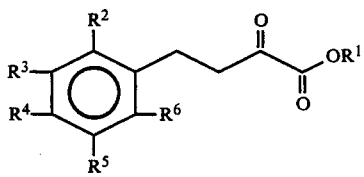

wherein
R$^1$ is H or C$_1$-C$_4$ alkyl; and
R$^2$-R$^6$ can be the same or different and are hydrogen, C$_1$-C$_6$ alkyl, aryl, halo (I, Cl, Br) nitro, hydroxy, alkoxy, phenoxy or nitrile,
which process comprises sequentially:
(a) condensing an aryl aldehyde with a pyruvate to obtain an unsaturated α-keto acid;
(b) esterifying said unsaturated α-keto acid with a C$_1$-C$_4$ alkyl chloroformate to obtain an unsaturated α-keto ester; and,
(c) reducing said unsaturated α-keto acid or unsaturated α-keto ester with hydrogen in the presence of a heterogeneous catalyst to obtain a compound of formula I,
said condensation, esterification and reduction being carried out sequentially and continuously without isolation of said unsaturated α-keto acid and said unsaturated α-keto ester intermediates.

2. The process of claim 1 wherein a condensing agent is used and is a member selected from the group consisting of potassium hydroxide, sodium hydroxide or calcium hydroxide.

3. The process of claim 1 wherein said pyruvate is a member selected from the group consisting of potassium pyruvate, sodium pyruvate or calcium pyruvate.

4. The process of claim 1 wherein said alkyl chloroformate is ethyl chloroformate.

5. The process of claim 1 wherein said heterogeneous catalyst is palladium hydride.

6. The process of claim 1 wherein said esterification is carried out under an inert atmosphere.

7. The process of claim 1 wherein said reduction is carried out at a pressure of from about 5 p.s.i. to about 30 p.s.i.

8. The process of claim 1 wherein said R$^2$-R$^6$ substituents are electron donating groups and said process temperature is from about 10° C. to about 25° C.

9. The process of claim 1 wherein said R$^2$-R$^6$ substituents are hydrogen or electron withdrawing groups and said process temperature is from about 0° C. to about 5° C.

10. The process of claim 1 wherein said unsaturated α-keto ester is isolated and recovered by evaporating the solvent and purifying the ester by distillation.

11. The process of claim 3 wherein said pyruvate is sodium pyruvate.

12. The process of claim 7 wherein said pressure is from about 10 p.s.i. to about 15 p.s.i.

13. The process of claim 8 wherein said electron donating groups are members selected from hydroxy, alkyl, alkoxy, phenoxy or aryl.

14. The process of claim 9 wherein said electron withdrawing groups are members selected from halo (I, Cl, Br) nitro or nitrile.

15. A continuous, non-isolation process for preparing benzylpyruvic acids and esters having the formula.

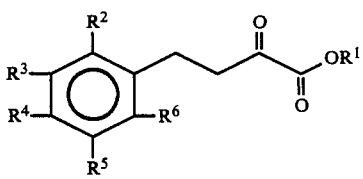

wherein
R$^1$ is H or C$_1$-C$_4$ alkyl; and,
R$^2$-R$^6$ can be same or different and are hydrogen, C$_1$-C$_6$ alkyl, aryl, halo (I, Cl, Br) nitro, hydroxy, alkoxy, phenoxy or nitrile,
which process comprises sequentially
(a) condensing an aryl aldehyde and a pyruvate selected from the group consisting of potassium pyruvate, sodium pyruvate, and calcium pyruvate, with a condensing agent selected from the group consisting of potassium hydroxide, sodium hydroxide or calcium hydroxide to obtain an unsaturated α-keto acid;
(b) esterifying said unsaturated α-keto acid under an inert atmosphere with ethyl chloroformate to obtain an unsaturated α-keto ester; and,
(c) reducing said unsaturated α-keto acid or said unsaturated α-keto ester with hydrogen in the presence of a palladium hydride catalyst at a pressure of from about 5 p.s.i. to about 30 p.s.i. to obtain a compound of formula I,
said condensation, esterification and reduction being carried out sequentially and continuously without isolation of said unsaturated α-keto acid and said unsaturated α-keto ester intermediates.

16. The process of claim 15 wherein said condensing agent is sodium hydroxide.

17. The process of claim 15 wherein said pyruvate is sodium pyruvate.

18. The process of claim 15 wherein said pressure is from about 10 p.s.i. to about 15 p.s.i.

19. The process of claim 15 wherein said R$^2$-R$^6$ substituents are electron donating groups and said process temperature is from about 10° C. to about 25° C.

20. The process of claim 15 wherein said R$^2$-R$^6$ substituents are hydrogen or electron withdrawing groups and said process temperature is from about 0° C. to about 5° C.

21. The process of claim 15 wherein said unsaturated α-keto ester is isolated and recovered by evaporating the solvent and purifying the ester by distillation.

22. The process of claim 19 wherein said electron donating groups are members selected from hydroxy, alkyl, alkoxy, phenoxy or aryl.

23. The process of claim 20 wherein said electron withdrawing groups are members selected from halo (I, Cl, Br) nitro or nitrile.

24. A continuous, non-isolation process for preparing benzylpyruvic acids and esters having the formula

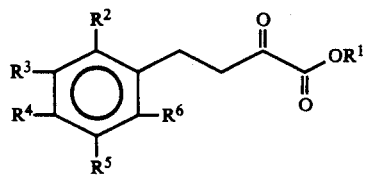

wherein
$R^1$ is H or $C_1$–$C_4$ alkyl; and,
$R^2$–$R^6$ can be same or different and are hydrogen, $C_1$–$C_6$ alkyl, aryl, halo (I, Cl, Br) nitro, hydroxy, alkoxy, phenoxy or nitrile,
which process comprises sequentially
(a) condensing an aryl aldehyde and sodium pyruvate with sodium hydroxide to obtain an unsaturated α-keto acid;
(b) esterifying said unsaturated α-keto acid under an inert atmosphere with ethyl chloroformate to obtain an unsaturated α-keto ester; and,
(c) reducing said unsaturated α-keto acid or said unsaturated α-keto ester with hydrogen in the presence of a palladium hydride catalyst at a pressure of from about 10 p.s.i. to about 15 p.s.i. to obtain a compound of formula I,
said condensation, esterification and reduction being carried out sequentially and continuously without isolation of said unsaturated α-keto acid and said unsaturated α-keto ester intermediates.

25. The process of claim 24 wherein said $R^2$–$R^6$ substituents are electron donating groups and said process temperature is from about 10° C. to about 25° C.

26. The process of claim 24 wherein said $R^2$–$R^6$ substituents are hydrogen or electron withholding groups and said process temperature is from about 0° C. to about 5° C.

27. The process of claim 24 wherein said unsaturated α-keto ester is isolated and recovered by evaporating the solvent and purifying the ester by distillation.

28. The process of claim 25 wherein said electron donating groups are members selected from hydroxy, alkyl, alkoxy, phenoxy or aryl.

29. The process of claim 26 wherein said electron withholding groups are members selected from halo (I, Cl, Br) nitro or nitrile.

* * * * *